United States Patent [19]
Shibamoto et al.

[11] Patent Number: 5,938,817
[45] Date of Patent: Aug. 17, 1999

[54] GAS CHROMATOGRAPH

[75] Inventors: Shigeaki Shibamoto, Kyoto; Koji Omiya, Shiga, both of Japan

[73] Assignee: Shimadzu Corporation, Kyoto, Japan

[21] Appl. No.: 08/984,416

[22] Filed: Dec. 3, 1997

[30] Foreign Application Priority Data

Jan. 30, 1997 [JP] Japan ................................. 9-032951

[51] Int. Cl.⁶ .............................................. B01D 15/08
[52] U.S. Cl. .............................. 95/23; 95/89; 96/102; 96/105; 73/23.24; 73/23.36
[58] Field of Search .................. 73/23.22, 23.24, 73/23.27, 23.36, 23.41, 23.42; 95/22, 89, 23; 96/102, 105

[56] References Cited

U.S. PATENT DOCUMENTS

| | | | |
|---|---|---|---|
| 3,858,435 | 1/1975 | Stevens | 96/102 X |
| 4,230,464 | 10/1980 | Bonmati et al. | 95/22 |
| 4,820,317 | 4/1989 | Fahey | 95/22 |
| 4,976,750 | 12/1990 | Munari | 96/102 X |
| 4,994,096 | 2/1991 | Klein et al. | 96/102 X |
| 5,032,151 | 7/1991 | Klein et al. | 95/89 X |
| 5,108,466 | 4/1992 | Klein et al. | 95/22 X |
| 5,163,979 | 11/1992 | Patrick et al. | 96/102 X |
| 5,391,221 | 2/1995 | Fukushima et al. | 95/89 X |
| 5,431,712 | 7/1995 | Henderson et al. | 95/22 |
| 5,476,000 | 12/1995 | Henderson et al. | 95/22 X |
| 5,531,959 | 7/1996 | Johnson et al. | 96/102 X |
| 5,545,252 | 8/1996 | Hinshaw et al. | 95/22 X |
| 5,567,227 | 10/1996 | Henderson | 95/22 |
| 5,759,234 | 6/1998 | Munari et al. | 95/89 X |
| 5,803,951 | 9/1998 | Wada et al. | 95/22 |

*Primary Examiner*—Robert Spitzer
*Attorney, Agent, or Firm*—Majestic, Parsons, Siebert & Hsue P.C.

[57] ABSTRACT

A gas chromatograph has a sample vaporization chamber connected to a column for vaporizing a liquid sample injected therein and introducing this vaporized liquid sample with a carrier gas into the column. There is also a flow rate control device for controlling the flow rate of the carrier gas either as it is being supplied into the vaporization chamber or as it is being discharged from the vaporization chamber through a discharge route other than the column for keeping the gas pressure approximately constant inside the vaporization chamber. A leakage detector detects a leakage of gas from the vaporization chamber on the basis of either a target value set for the flow rate control device or a monitored value of the flow rate. A warning device outputs a warning when a gas leakage is detected by the leakage detecting device.

10 Claims, 3 Drawing Sheets

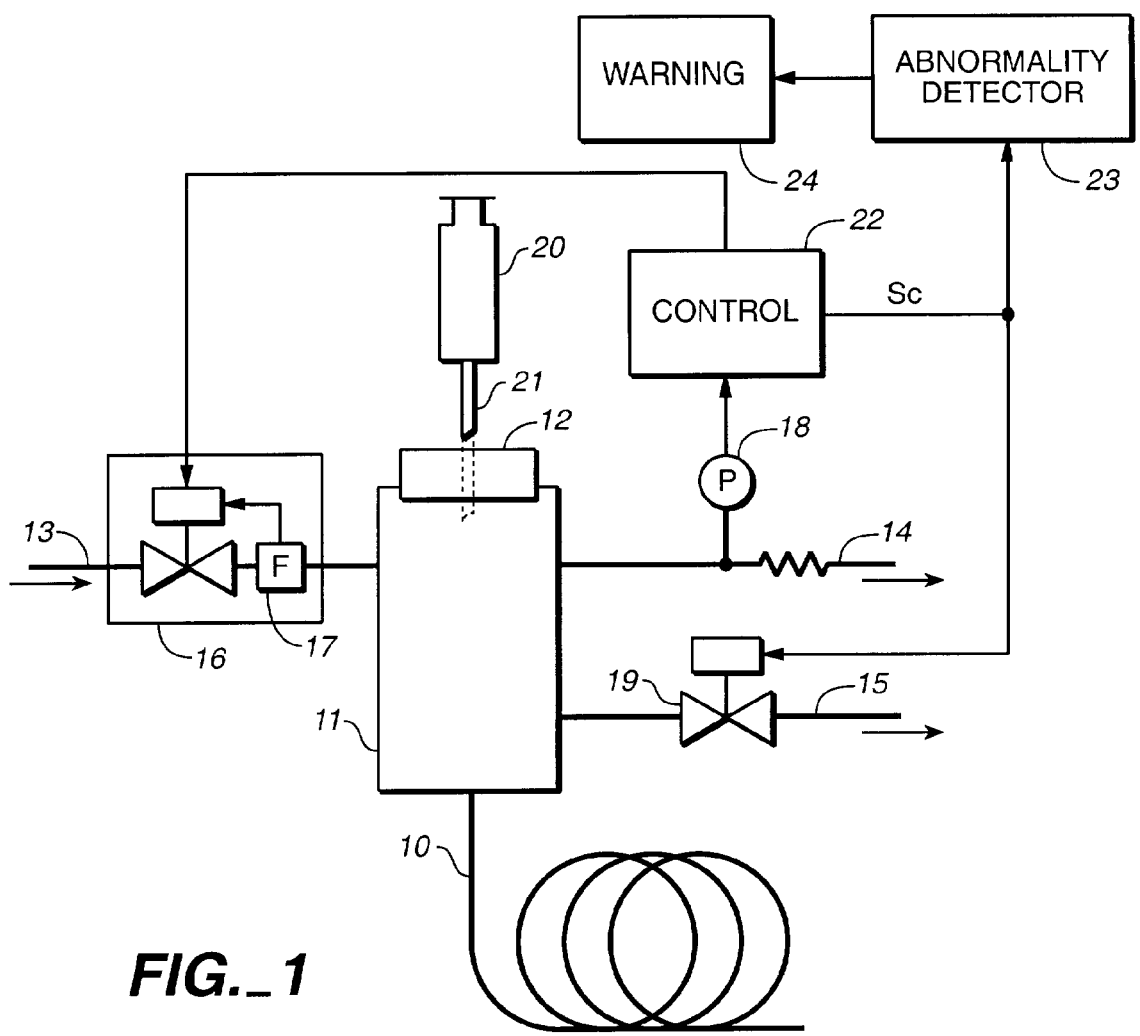
FIG._1
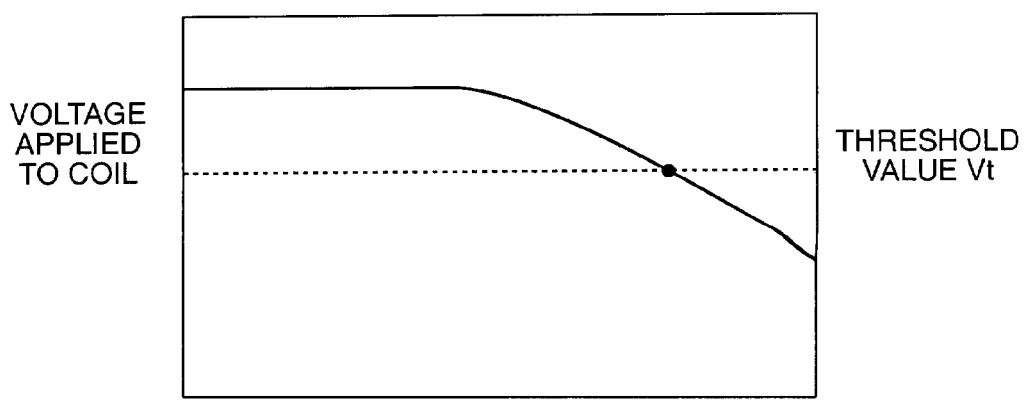
FIG._2

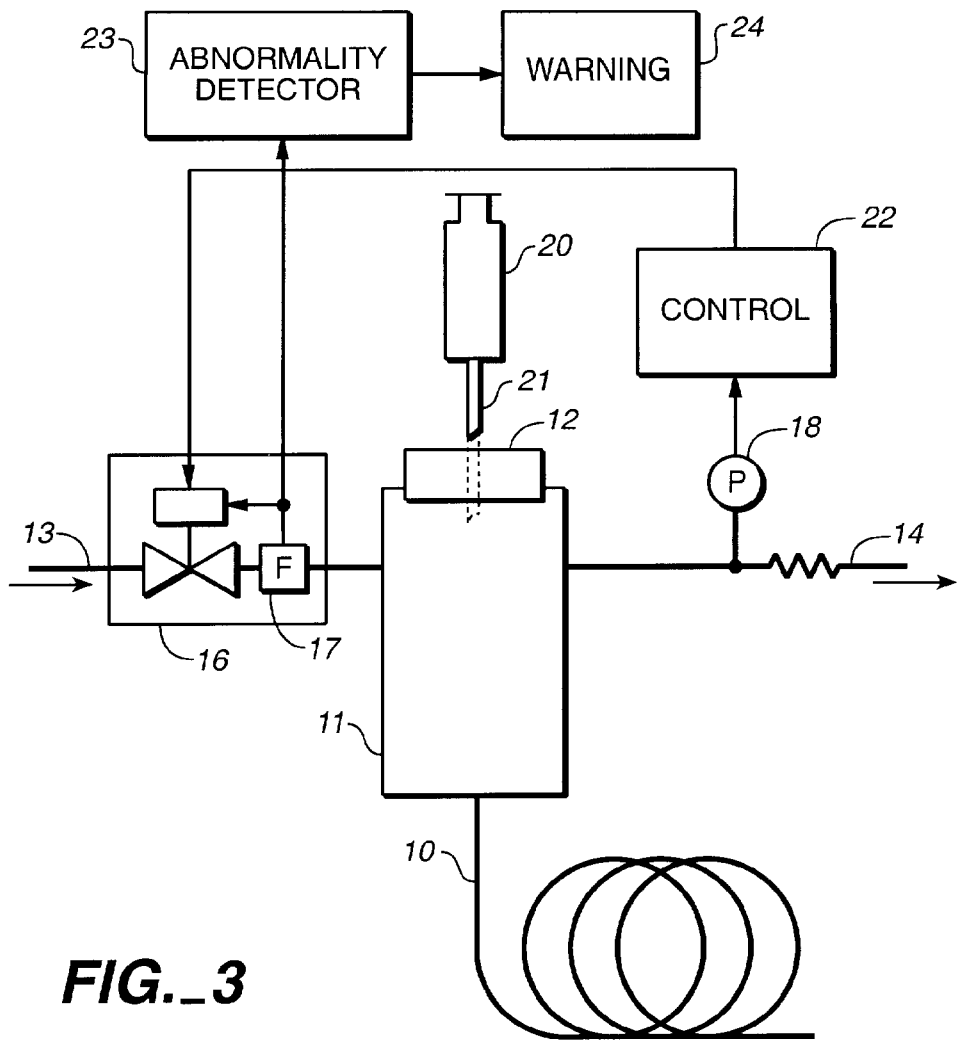
FIG._3
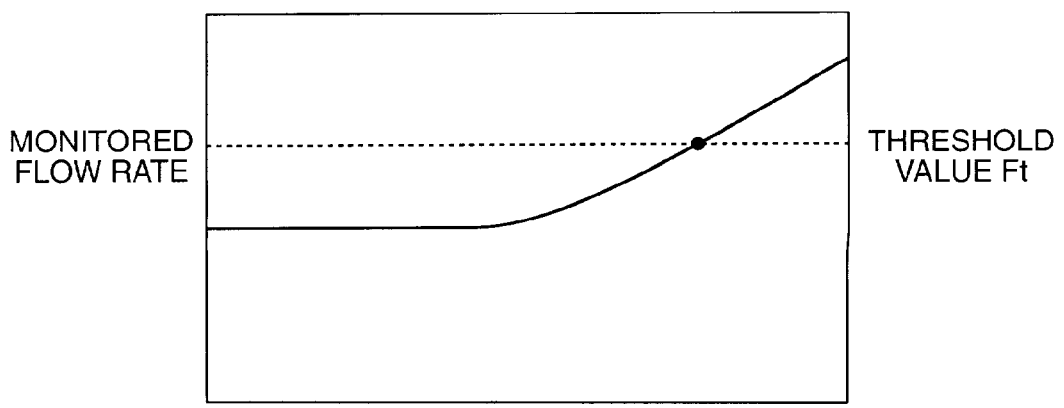
FIG._4

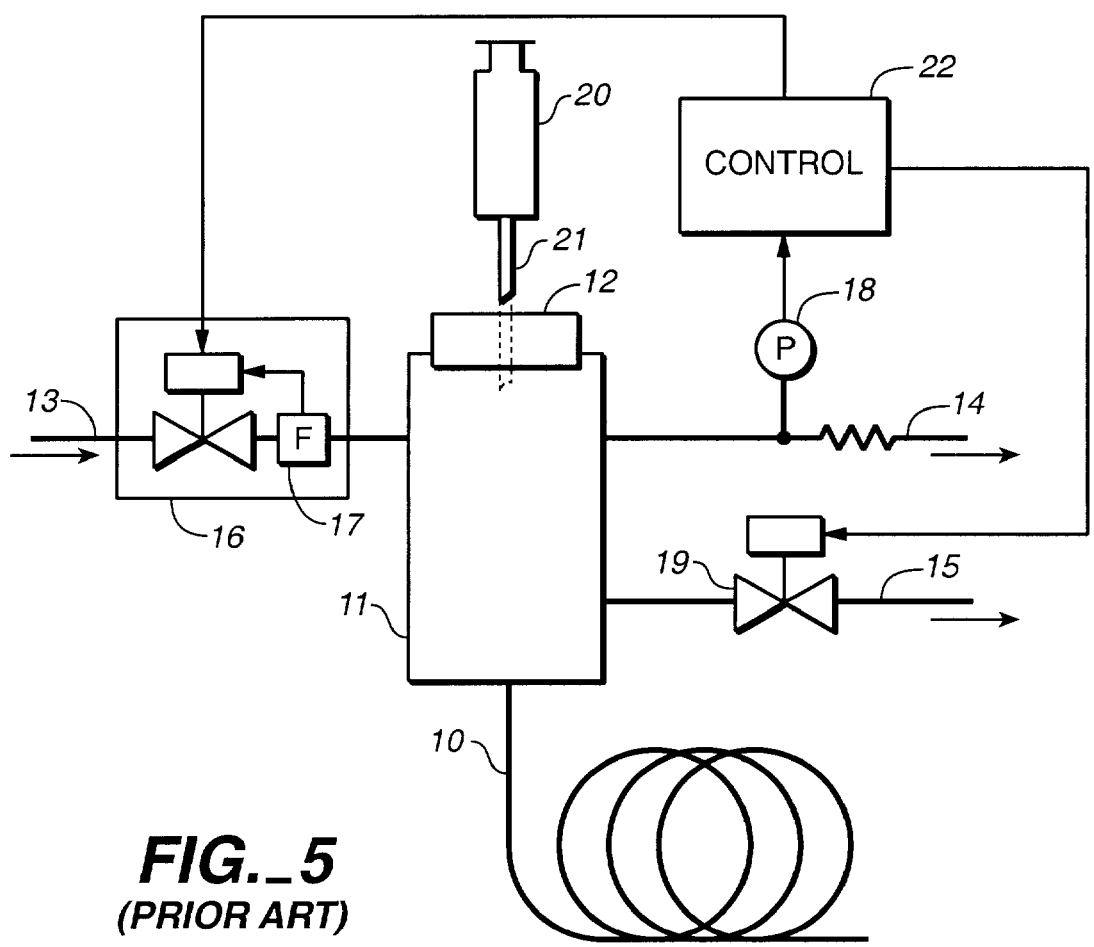
FIG._5
*(PRIOR ART)*

GAS CHROMATOGRAPH

BACKGROUND OF THE INVENTION

This invention relates to a gas chromatograph and more particularly to the sample intake part of a gas chromatograph.

FIG. 5 shows schematically a portion of an ordinary gas chromatograph including its sample intake part. A septum 12 made of a silicone rubber material is provided at the top of a sample vaporization chamber 11 at the entrance to a column 10, and a carrier gas flow route 13 for introducing a carrier gas, a purge route 14 for discharging components generated by the septum 12 and a split route 15 for discharging a portion of the sample injected into the sample vaporization chamber 11 together with the carrier gas are each connected to the side of this sample vaporization chamber 11. A mass flow controller 16 for controlling the flow rate of the carrier gas such as He is contained in the carrier gas flow route 13, a pressure sensor 18 is contained in the purge route 14, and a control valve 19 for controlling the flow rate of the discharge gas is contained in the split route 15. Since there is hardly any gas resistance between the pressure sensor 18 and the vaporization chamber 11, the pressure detected by this pressure sensor 18 may be considered the same as the gas pressure inside the sample vaporization chamber. Thus, a control unit 22 monitors the gas pressure inside the sample vaporization chamber 11 through the pressure sensor 18 and controls the mass flow controller 16 and the control valve 19 such that this gas pressure remains constant and that the ratio of the amount of carrier gas supplied into the sample vaporization chamber 11 and that of the gas flowing into the column 10 (or the split ratio) will be kept at a specified level such as 100:1.

When a liquid sample is injected into the sample vaporization chamber 11, a needle 21 attached to a syringe 20 is inserted through the septum 12. The liquid sample which is dropped is quickly vaporized and carried into the column 10, riding the stream of the carrier gas, while an excess portion of the gas is discharged outside through the split route 15. The septum 12 is made of an elastic material such that the opening created when the needle 21 is inserted therethrough is quickly closed as soon as the needle 21 is pulled out. If its elastic property has deteriorated after a long period of use or the number of openings has increased after a large number of use, the opening ceases to be closed completely and the gas inside the sample vaporization chamber 11 may begin to leak out. If a chromatographic analysis is carried out under such a condition, the retention time which indicates the time of appearance of a peak in a chromatogram may be displaced or the peak area may become smaller, thereby making it difficult to obtain a reliable analytical result.

For this reason, the septum 12 should be replaced periodically with a new one. In general, however, it is left to the user or a supervisor in charge of the chromatograph to keep track of the time for exchanging the septum 12. Thus, it is often forgotten to put a new septum and analyses are carried out under a less than perfect condition. When an automatic injector is used to carry out automatic analyses of many samples continuously, in particular, a gas leakage is likely to happen, wasting many hours of time and precious samples.

SUMMARY OF THE INVENTION

It is therefore an object of this invention in view of the above to provide an improved chromatograph adapted to automatically detect a time for exchanging its septum such that the user can be prevented from forgetting to exchange it with a new one.

A gas chromatograph according to this invention, with which the above and other objects can be accomplished may be characterized not only as having a sample vaporization chamber connected to a column for vaporizing a liquid sample injected therein and introducing this vaporized liquid sample with a carrier gas into the column but also as comprising flow rate control means for controlling the flow rate of the carrier gas either as it is being supplied into the vaporization chamber or as it is being discharged from the vaporization chamber through a discharge route other than the column for keeping the gas pressure approximately constant inside the vaporization chamber, leakage detecting means for detecting a leakage of gas from the vaporization chamber on the basis of either a target value set for the flow rate control means or a monitored value of the flow rate, and warning means for outputting a warning when a gas leakage is detected by the leakage detecting means. The flow rate control means may be adapted to control one or more of adjusting or controlling devices such as a flow rate controller for directly controlling the flow rate of the carrier gas being supplied into the vaporization chamber, a pressure controller for adjusting the pressure of the carrier gas being supplied to the vaporization chamber, a valve or a flow resistor for adjusting the flow rate of the carrier gas being discharged from the vaporization chamber through a flow route other than the column.

In the case of a gas chromatograph adapted to discharge the gas from the vaporization chamber through a split route, the opening of the valve provided in the split route is usually adjusted in order to maintain the pressure constant inside the vaporization chamber. In such a case, the leakage detecting means may be adapted to detect a leakage on the basis of a control target value set for such a valve. As this valve is controlled in order to maintain a constant pressure inside the vaporization chamber, the valve is controlled so as to reduce its opening as the gas leakage increases. When a new septum is installed, an initial value of this control target value is stored, and the leakage detector detects a leakage at the time of a later analysis if the control target value is found to be lower than this stored initial value by more than a specified value.

In the case of a gas chromatograph without a split route, the flow rate of the carrier gas is usually controlled as it is being supplied into the vaporization chamber in order to maintain the gas pressure constant inside the vaporization chamber. In such a case, the leakage detecting means may be adapted to detect a leakage on the basis of a monitored flow rate value of the gas. As a flow rate controller is adjusted in order to maintain a constant pressure inside the vaporization chamber, the gas flow rate must be increased if the leakage increases. Thus, the initial value of the gas flow rate immediately after the septum has been exchanged is stored in a memory and a leakage is detected at the time of a later analysis if the monitored flow rate value of the gas reaches a specified value or increases by a specified value.

According to a gas chromatograph of this invention, a leakage of gas is automatically reported if the number of sample injection is increased and the gas leakage through the septum increases and comes to affect the results of the analyses. In other words, the user can learn exactly when the septum should be replaced with a new one. It now goes without saying that a gas chromatograph according to this invention can detect a gas leakage also through an O-ring of a silicone rubber material used for sealing a glass column.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a structural diagram of a portion of a gas chromatograph according to a first embodiment of this invention;

FIG. 2 is a graph showing the relationship between the voltage to be applied to the coil and the number of analyses by using the gas chromatograph shown in FIG. 1;

FIG. 3 is a structural diagram of a portion of another gas chromatograph according to a second embodiment of this invention;

FIG. 4 is a graph showing the relationship between the monitored flow rate value and the number of analyses by using the gas chromatograph shown in FIG. 3; and FIG. 5 is a structural diagram of a portion of a prior art gas chromatograph.

Throughout herein, like components are indicated by the same numeral and not repetitively described.

DETAILED DESCRIPTION OF THE INVENTION

FIGS. 1 and 2 show a gas chromatograph according to a first embodiment of this invention with a sample intake part of a back pressure control type having a split route. The basic structure of the sample intake part is the same as shown in FIG. 5 except the control unit 22 is adapted to transmit a control target value Sc both to the control valve 19 and to a detector 23 of an abnormal condition. The abnormality detector 23 is for detecting a gas leakage, as will be described below, and to transmit a warning signal thereupon to a warning device 24. The warning device 24 may comprise a display lamp or a buzzer, adapted to display a warning or to make a warning sound when the warning signal from the detector 23 is received.

With the gas chromatograph thus structured, the mass flow controller 16 is controlled such that the carrier gas flow rate detected by a flow rate sensor 17 will be constant and that the carrier gas will always be sent into the sample vaporization chamber 11 at a constant rate. The control unit 22 serves to detect the gas pressure inside the sample vaporization chamber 11 through the pressure sensor 18 and to control the control valve 19 in the split route 15 such that a specified pressure for obtaining a specified split ratio can be maintained. If the control valve 19 is of the type having a coil and a flap such that the flap will open or close and its opening will change according to the voltage applied on the coil, the control unit 22 transmits to the control valve the magnitude of this voltage to be applied as the control target value Sc.

When the septum 12 has been replaced by a new product, the user carries out a specified initializing routine for the detection of gas leakage. After this initialization is carried out, the abnormality detector 23 reads in the control target value Sc at the time of the first analysis after the septum 12 has been replaced (preferably during a period when the sample is not being injected) and stores it in a memory (not shown) as an initial value. The threshold value for the identification of an abnormal condition due to a gas leakage is determined on the basis of the change or the ratio of the change in the voltage to be applied to the coil with respect to the initial value and is inputted by the user. This should be determined according to the purpose of the analysis. If a very accurate analysis is desired, the threshold should be set such that an abnormal condition can be detected even by a small change from the initial value. If only a rough analysis is sufficient, on the other hand, the allowable range of deviations from the initial value may be accordingly enlarged.

Every time a new analysis is carried out, the abnormality detector 23 reads in the control target value Sc and compares it with the initial value stored in the memory and the threshold value determined by an inputted value. FIG. 2 shows the relationship between the number of analyses which have been carried out by using the same septum and the voltage applied to the coil. As shown, the voltage applied to the coil hardly changes for a certain period after a new septum is installed but the gas leakage increases suddenly after the analysis has been repeated for a certain number of times. This means that the opening of the control valve 19 must be reduced in order to also reduce the discharge of gas through the control valve 19 such that a constant gas pressure can be maintained. Thereafter, the voltage to be applied to the coil gradually decreases as the gas leakage increases.

When the voltage to be applied to the coil comes down to the level of the threshold value Vt, the abnormality detector 23 transmits a warning signal to the warning device 24 to cause it, for example, to switch on a warning lamp. If this happens in the midst of an automatic analysis by means of an automatic injector, a different signal may be designed for interrupting the analysis by transmitting such a signal to the control unit for the automatic injector.

FIG. 3 shows another gas chromatograph according to a second embodiment of the invention with a sample intake part of the inlet pressure control type having no split route. With the gas chromatograph thus structured, the control unit 22 monitors the gas pressure inside the sample vaporization chamber 11 by means of the pressure sensor 18 and controls the flow rate of the mass flow controller 16 so as to maintain this gas pressure at a constant level.

The abnormality detector 23 monitors the gas flow rate by means of the flow rate sensor 17 of the mass flow controller 16. When a gas leakage occurs through the septum 12, it becomes necessary to supply more carrier gas into the vaporization chamber 11 in order to maintain a constant pressure therein. Thus, the monitored gas flow rate increases as shown in FIG. 4 as the gas leakage increases. The abnormality detector 23 sends a warning signal to the warning device 24 when the monitored value of the flow rate reaches a predetermined threshold value Ft, for example, to switch on a warning lamp.

Although the invention has been described above with reference to only two embodiments but these examples are not intended to limit the scope of the invention. Many modifications and variations are possible within the scope of the invention. For example, the control target value or the monitored flow rate value may be stored in the memory for each analysis. When the next analysis is carried out, the new control target value or the new monitored flow rate value is compared with the stored value from the previous analysis. An abnormal situation may be detected, depending on whether the difference is greater than a predetermined threshold value.

In the case of an automatic analysis by means of an automatic injector, it is frequently the case that nobody is near the chromatograph during a series of analyses. Thus, if the gas leakage reaches an abnormal level in such a case, the analyses will be stopped in the middle. Since the septum could be exchanged before the start of a series of analyses with an automatic injector if only the occurrence of an abnormal condition could be detected ahead of time. Thus, the abnormality detector 23 shown in FIGS. 1 and 3 may be adapted such that the voltage value or the monitored flow rate value for each analysis is stored and that, prior to the start of a series of analyses with an automatic injector, the change in the voltage value or the monitored flow rate value is predicted on the basis of the past values. Thus, it may be possible to predict if the actual voltage or monitored flow rate value will reach the threshold value during the proposed series of analyses. In summary, all such modifications and variations that may be apparent to a person skilled in the art are intended to be within the scope of the invention.

What is claimed is:

1. A method of operating a gas chromatograph having a column connected to a vaporization chamber, said method comprising the steps of:

installing a septum to said chromatograph;

storing a target flow rate value corresponding to said septum;

controlling and monitoring flow rate of a carrier gas while causing said carrier gas to flow through said vaporization chamber into said column;

making a comparison between the monitored flow rate and said target flow rate value; and detecting a gas leakage based on a result of said comparison.

2. The method of claim 1 wherein said flow rate of the carrier gas is controlled as said carrier gas is being supplied into said vaporization chamber.

3. The method of claim 2 further comprising the step of predicting an abnormal condition from past monitored values of the flow rate of said carrier gas.

4. The method of claim 1 wherein said flow rate of the carrier gas is controlled as said carrier gas is being discharged from said vaporization chamber through a discharge route other than said column.

5. The method of claim 4 further comprising the step of predicting an abnormal condition from past target values which were set before.

6. A gas chromatograph comprising:

a sample vaporization chamber connected to a column for vaporizing a liquid sample injected therein and introducing the vaporized liquid sample with a carrier gas into said column;

flow rate control means for controlling and monitoring the flow rate of said carrier gas selectably either as said carrier gas is being supplied into said vaporization chamber or as said carrier gas is being discharged from said vaporization chamber through a discharge route other than said column for keeping the gas pressure approximately constant inside said vaporization chamber;

means for storing and outputting a target value corresponding to a septum installed on said chromatograph;

leakage detecting means for detecting a leakage of gas from said vaporization chamber on the basis of a comparison between said target value and a monitored value of said flow rate; and warning means for outputting a warning when said leakage detecting means detects a leakage of gas.

7. The gas chromatograph of claim 6 wherein said flow rate control means controls the flow rate of said carrier gas as said carrier gas is being supplied into said vaporization chamber.

8. The gas chromatograph of claim 7 wherein said leakage detecting means serves to predict an abnormal condition on the basis of past monitored values of said flow rate.

9. The gas chromatograph of claim 6 wherein said flow rate control means controls the flow rate of said carrier gas as said carrier gas is being discharged from said vaporization chamber through a discharge route other than said column.

10. The gas chromatograph of claim 9 wherein said leakage detecting means serves to predict an abnormal condition on the basis of past target values set for said flow rate control means.

* * * * *